United States Patent
Schorn et al.

(10) Patent No.: US 9,541,506 B2
(45) Date of Patent: Jan. 10, 2017

(54) CONTAINER INSPECTION ARRANGEMENT FOR INSPECTING GLASS AND/OR PLASTIC CONTAINERS AND A METHOD OF INSPECTING GLASS AND/OR PLASTIC CONTAINERS

(71) Applicants: Wolfgang Schorn, Hoenningen (DE); Carsten Buchwald, Sinzig (DE)

(72) Inventors: Wolfgang Schorn, Hoenningen (DE); Carsten Buchwald, Sinzig (DE)

(73) Assignee: KHS GmbH, Dortmund (DE)

( * ) Notice: Subject to any disclaimer, the term of this patent is extended or adjusted under 35 U.S.C. 154(b) by 16 days.

(21) Appl. No.: 14/626,337

(22) Filed: Feb. 19, 2015

(65) Prior Publication Data
US 2015/0308964 A1    Oct. 29, 2015

Related U.S. Application Data

(63) Continuation-in-part of application No. PCT/EP2013/002382, filed on Aug. 8, 2013.

(30) Foreign Application Priority Data

Aug. 20, 2012    (DE) .......................... 10 2012 016 342

(51) Int. Cl.
  *G01N 21/90*    (2006.01)
(52) U.S. Cl.
  CPC .......... *G01N 21/9072* (2013.01); *G01N 21/90* (2013.01); *G01N 21/9054* (2013.01); *G01N 21/9081* (2013.01)
(58) Field of Classification Search
  CPC  G01N 21/9072; G01N 21/90; G01N 21/9054; G01N 21/9081; G01N 2033/0081
  (Continued)

(56) References Cited

U.S. PATENT DOCUMENTS 5,405,015 A * 4/1995 Bhatia .................... B07C 5/3408
                                                 209/524
5,926,268 A * 7/1999 Bonewitz .............. B07C 5/3416
                                                 356/240.1
(Continued)

FOREIGN PATENT DOCUMENTS

CN        1111351 A    11/1995
CN        1099588 C     1/2003
(Continued)

OTHER PUBLICATIONS

German Office Action 10 2012 016 342.8 dated Jun. 19, 2013.
(Continued)

*Primary Examiner* — Sang Nguyen
(74) *Attorney, Agent, or Firm* — Nils H. Ljungman & Associates

(57) ABSTRACT

A container inspection arrangement for inspecting glass and/or plastic containers, and a method of inspecting glass and/or plastic containers. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

20 Claims, 7 Drawing Sheets

(58) Field of Classification Search
USPC .......... 356/239.1, 239.4, 239.5, 239.6, 240.1
See application file for complete search history.

(56) References Cited

U.S. PATENT DOCUMENTS

| | | | |
|---|---|---|---|
| 7,238,930 B2* | 7/2007 | Watanabe | G01B 11/24 250/223 B |
| 2004/0263838 A1* | 12/2004 | Diehr | B07C 5/3408 356/239.1 |
| 2008/0158554 A1 | 7/2008 | Niedermeier | |
| 2011/0025840 A1* | 2/2011 | Fiegler | G01N 21/9027 348/127 |
| 2011/0102782 A1* | 5/2011 | Wiemer | G01N 21/15 356/239.4 |

FOREIGN PATENT DOCUMENTS

| | | |
|---|---|---|
| CN | 1708683 A | 12/2005 |
| DE | 103 10 273 | 9/2004 |
| DE | 10 2004 051 961 | 5/2006 |
| DE | 10 2005 057 872 | 6/2007 |
| DE | 10 2006 062575 | 3/2008 |
| DE | 10 2010 018 824 | 11/2011 |
| EP | 0 894 544 | 2/1999 |
| EP | 2 229 582 | 9/2010 |
| GB | 2173589 | 10/1986 |
| JP | 04216445 A * | 8/1992 |
| JP | H04216445 | 8/1992 |
| JP | 2000193606 | 7/2000 |
| JP | 2006 201003 | 8/2006 |
| JP | 2006201003 A | 8/2006 |
| RU | 2017142 | 7/1994 |
| WO | WO 2009/056188 | 5/2009 |

OTHER PUBLICATIONS

International Search Report PCT/EP2013/002382 dated Oct. 25, 2013, and English translation thereof.
International Preliminary Report dated Feb. 24, 2015, and English translation thereof.

* cited by examiner

CONTAINER INSPECTION ARRANGEMENT FOR INSPECTING GLASS AND/OR PLASTIC CONTAINERS AND A METHOD OF INSPECTING GLASS AND/OR PLASTIC CONTAINERS

CONTINUING APPLICATION DATA

This application is a Continuation-In-Part application of International Patent Application No. PCT/EP2013/002382, filed on Aug. 8, 2013, which claims priority from Federal Republic of Germany Patent Application No. 10 2012 016 342.8, filed on Aug. 20, 2012. International Patent Application No. PCT/EP2013/002382 was pending as of the filing date of this application. The United States was an elected state in International Patent Application No. PCT/EP2013/002382.

BACKGROUND

1. Technical Field

The present application relates to a container inspection arrangement for inspecting glass and/or plastic containers, and a method of inspecting glass and/or plastic containers.

2. Background Information

Background information is for informational purposes only and does not necessarily admit that subsequently mentioned information and publications are prior art.

The present application relates to an inspection device for inspecting containers wherein the inspection device comprises at least one transport path and has at least one illumination unit, one camera and one optical structure, and wherein a transparent hollow body is provided which is mounted so as to be rotatable about a center axis, said hollow body being arranged underneath a container to be inspected.

Containers in the meaning of the present application are for example bottles, cans, tubes, pouches, in each case made of glass and/or plastic, and for example also PET bottles, but also other packaging means, for example those suitable for filling with liquid or viscous products.

Devices for the illumination and inspection of container bases are known. Some inspection machines transport containers in a suspended manner over an illumination unit. The illumination unit itself is a rectangular block which shines through the containers from below. In principle, these devices are reliable and suitable, and must or should be simply be cleaned relatively often to essentially guarantee or promote reliable operation and meaningful measured values.

In some devices, the conveyor may be illuminated from below, on which conveyor the bottles to be inspected stand, and the conveyor may be transparent and made as a turntable. Here, the contamination on the illumination unit itself is reduced, but solid and liquid adhesions on the transparent turntable itself likewise require or desire regular cleaning.

Some inspection devices for inspecting containers, for example bottles, may comprise at least one transport path for transporting containers to and away from an illumination unit, an optical measuring unit and a control unit, wherein the illumination unit is enclosed by a transparent hollow body which is mounted so as to be rotatable about a center axis and the hollow body can be motor-driven directly or by suitable operative connections. The hollow body is in one example a pipe which is made of a material or a mix of materials which is transparent for beams of wavelengths in the optically visible range, in the infrared range and/or in the ultraviolet range, wherein the material is at least partially transparent for these beams. In such an inspection device, an internal inspection is carried out using a camera from above through the mouth of the container in the direction of the base. In an embodiment such as this, however, not all of the internal areas of the container, for example a bottle, can be inspected, as shown in FIG. 1 of the present application, so that not all defects or contamination F1 and F2 can be perfectly or substantially perfectly detected.

OBJECT OR OBJECTS

Thus, a purpose of the present application is to provide a container inspection device that addresses the inaccuracies in inspection discussed above.

SUMMARY

According to the present application, the object is resolved by an inspection device, wherein the optical structure relative to the rotatable transparent hollow body is arranged rigidly inside the latter in such a way that the containers to be inspected can be inspected by means of the at least one camera through the container base in the direction of the mouth.

According to the present application, an inspection device is made available with which the containers, in one possible embodiment bottles, are inspected from below through the closed base. In this way, the areas which could not previously be inspected are accessible for the inspection device so that a safe and reliable statement with regard to the inspection result is possible.

It is beneficial here if the illumination unit shines light on the containers from outside, wherein area lighting can be used. Thus, defects in the internal side wall of the container or the bottle can be detected. Alternatively, or in combination with the area lighting, a ring light illumination is also possible, which shines on the container from below in order to be able to detect defects in the base, wherein the illumination unit is then usefully arranged inside the hollow body. The illumination units or light sources can differ with regard to their emitted light colors. It is useful to inspect the base by the so-called dark field method, and hence the illumination unit is accordingly located inside the hollow body. The side wall inspection by means of the area lighting can be carried out by the so-called transmitted light method.

In one possible case where a bottle is to be inspected which has walls which are for example very heavily decorated or even painted, then illumination from the inside can be useful.

It is beneficial if the at least one illumination unit is arranged inside the rotatable transparent hollow body, wherein an embodiment as a ring light illumination would be beneficial which concentrically comprises the optical axis of the optical structure. The illumination unit is thereby likewise arranged rigidly or in a stationary manner inside the hollow body, like the optical structure.

It is beneficial for the purposes of the present application if the optical structure has lens and mirror systems. The mirror system or systems can also have semi-transparent mirrors. Optical filters can also be arranged before the camera or cameras, which allow for the selection, for example, of certain wavelengths, colors or spectra.

The optical structure is arranged so that its optical axis is arranged parallel to, substantially parallel to, or intermittently congruent with the center vertical axis of the container to be inspected. The containers are transported continuously past the optical structure so that, at a certain transport position, its optical axis is congruent with or otherwise parallel or substantially parallel to the vertical axis of the container. It is also useful if the container to be inspected is transported along the axial transport direction rotating about its vertical axis, which for example can be achieved with transport elements or lifting belts arranged on the side, which are at a different speed from each other so that the container is set in rotation about its vertical axis. By means of the mirrors or by means of the semi-transparent mirrors, the optical light beam can be diverted, which per se is known.

For the purposes of the present application, an inspection from below means that the optical structure arranged rigidly in the hollow body is arranged underneath the container to be inspected, wherein mirrors or semi-transparent mirrors divert the light beam. Thus a camera with its optical axis can be congruent with an axis of rotation of the hollow body. The camera can thus be arranged at the side next to the hollow body. The camera can however also be arranged directly underneath the hollow body. However, it is also possible to arrange a camera above or also to the side above the hollow body and/or the container to be inspected, wherein the light beam of the optical structure arranged underneath the container to be inspected can be diverted appropriately for the camera by means of mirrors. In this way, many arrangement positions of the camera arise, wherein the optical structure is always or substantially always or sometimes arranged inside the hollow body.

In a one possible embodiment, two cameras can be provided, of which one camera has its optical axis congruent with the axis of rotation, wherein the second camera is arranged directly below the optical structure, but outside the hollow body. In a further embodiment, a semi-transparent mirror can then be used, which diverts the light beam to the camera arranged at the side and at the same time lets it through to the camera arranged underneath.

In one possible embodiment, the rotatable transparent hollow body is made of a plastic, e.g. of PTFE or acrylic glass, or of tempered glass, wherein the materials are named naturally by way of example. It is also possible if the hollow body which can also be described as a glass cylinder is self-cleaning, for which cleaning units can possibly be used.

An improvement to the inspection device comprises a diffusion element being arranged between the hollow body and the upper side of the illumination unit or of the ring light illumination, wherein said diffusion element leads to a balancing of illumination means. Moreover, upper side of the illumination unit means the side which faces the container to be inspected or the bottle to be inspected and through which the emission occurs. The corresponding counterpart is described as the underside.

The diffusion element can basically be of a flat level shape, but it has turned out that it is possibly arched and arranged between the hollow body and the upper side of the illumination element, wherein the materials and the manufacturing processes are basically known for diffusion elements of this kind. The diffusion element can possibly be made in an annular shape.

A further improvement to the inspection device can be achieved if a polarization filter is provided which possibly is arranged between the hollow body and the upper side of the illumination unit and possibly likewise has an arched and also annular shape. The use of polarization filters or circular polarization filters for inspection machines is known and is used for example to achieve a reliable detection of transparent solids, for example films, in the container.

Suitable polarization filters are made for example of film of polyvinyl alcohol, which can be stabilized mechanically by means of a coating of cellulose acetate butyrate on both sides. Further materials are basically known and can be used depending on the possible application.

On the inspection device, in a variation of the device on the hollow body, as already mentioned above, a cleaning unit can be arranged which is possibly arranged underneath the illumination unit but outside the light beam of the camera optionally arranged underneath. This cleaning unit can furthermore comprise a feed device. The feed device has outlets or nozzles for illuminating the outer surface of the hollow body and is suitable for gaseous or liquid media.

In an another possible variation, the cleaning unit comprises at least one take-off device which has mechanical scrapers in the form of brushes, sealing lips made of a flexible material, or suction elements, to remove solid or liquid adhesions from the surface of the hollow body. Due to the rotation of the hollow body, the adhesions are permanently or sequentially moved from the upper side, thus out of the inspection field, in the direction of the underside. There, if there is no camera optionally arranged underneath, regardless of the measuring and inspection operation, any suitable and necessary or desired wet and/or dry cleaning can take place. If the camera optionally arranged underneath is provided, the cleaning unit is then offset from it in the circumferential section outside the light beam of the camera or of the optical structure. It is also possible to monitor the hollow body itself to actuate the cleaning unit where cleaning is needed and/or desired. Means for this are known and hence this will not be explained in more detail here, although the components of the cleaning unit can be shifted in a possible manner to adapt to the camera optionally arranged underneath the optical structure. Thus, for example, a heating or drying blower can be arranged after a scraper in the direction of rotation before the optional camera.

The rotating hollow body of the inspection device can be open on at least one side for reasons of heat development and for the power supply. In this way, deposits can get into the inner surface and be transported into the inspection field. An improvement therefore comprises the cleaning unit projecting in such a way onto or into the hollow body that at least solid or liquid adhesions can be removed from the outer surface of the hollow body and possibly can also be removed from the inner surface. With a cylindrical hollow body, a cantilever, comprising suitable scrapers, can project into the interior and carry out cleaning work there.

In an alternative embodiment, the hollow body is closed on the front side too and connected to a gas pipe, by means of which during operation as intended, an inert gas, in one possible embodiment compressed air, can be routed into the interior of the hollow body. By maintaining a permanent or semi-permanent or temporary over-pressure in the interior of the hollow body, contamination of the inner surfaces can reliably be avoided and/or reduced and/or minimized. To allow a light beam to the camera optionally arranged at the side, the front faces are possibly likewise transparent.

With the present application, defects on the container base or on the bottle base can be detected which would be detected with difficulty with a pure transmitted light method in the event of an inspection from above, i.e. with a camera light beam through the mouth in the direction of the base. In at least one possible embodiment of the present application, with the present application however, PET cracks, the age and the wear of the container and also base fluting and imprints can be detected. In addition, defects are visible which, in an inspection from above through the narrow area of the mouth, it would not be possible to inspect due to the resulting light beam. This applies in one possible embodiment for the neck and shoulder region of the container or the bottle. Furthermore, with the present application, bottle imprints can be detected so that they can be clearly excluded from a defect image. Thus, defects and/or contamination underneath indentations, embossings and the shoulder can be very easily detected. Furthermore, for the purposes of quality assurance, a reliable or improved detection of the bottle seam and embossings is possible. Also, marks near the edges, e.g. circumferential marks, can be detected which were introduced e.g. during filling.

Thus, a method for inspecting containers is thus covered by the present application, with at least one or more illumination units and at least one camera, wherein the camera is oriented from below onto the base of the container. This can take place directly or by means of suitable mirrors. The substantial factor here is that the light beam of the camera passes through the container base to detect the inner surface of the container, for the detection of contamination, defects or such like. Moreover, this can serve additionally or supplementally, to ascertain the position and/or geometry of the mouth of the container and thus the symmetry of the container itself.

Moreover, the container is in one possible embodiment transported in a suspended manner, by being held clamped on lateral conveyor belts or secured in the neck area and moved by grippers or clamps.

In at least one possible embodiment of the present application, this inspection method is carried out with an inspection device according to one of the aforesaid embodiment variations.

Further developments, benefits and application possibilities of the present application arise also from the following description of examples of embodiments and from the figures. In this regard, characteristics described and/or illustrated individually or in any combination are categorically the subject of the present application, regardless of their inclusion in the claims or reference to them. The content of the claims is also an integral part of the description.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

In the various figures, the same parts are given the same reference symbols, and hence they are generally also described once.

Figure 1:
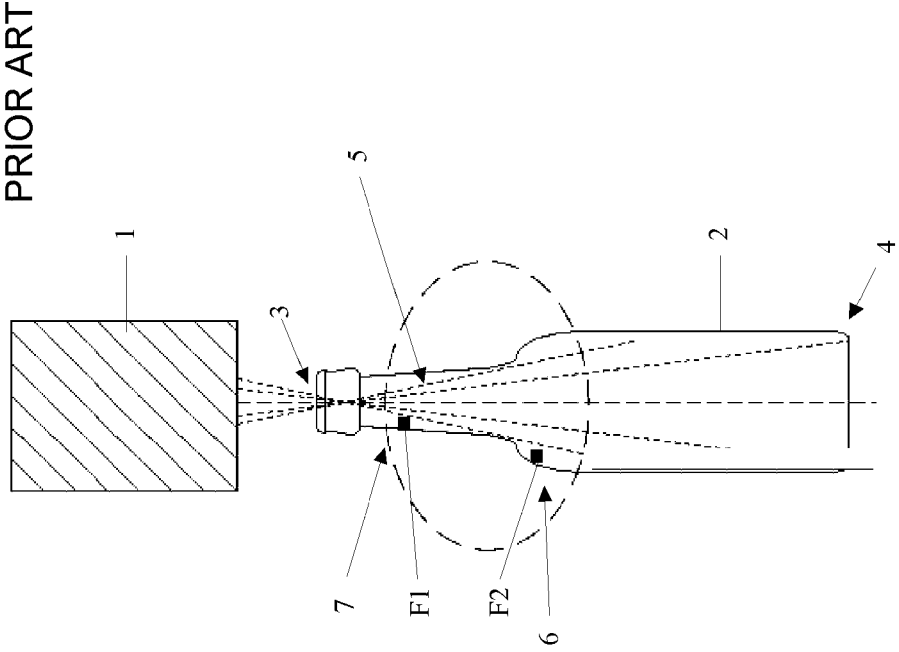
FIG. 1 shows an inspection device according to the prior art.

FIG. 1 shows an inspection operation according to the prior art in which, with an optical structure 1, a container 2 is inspected through a mouth 3 in the direction of the container base 4. It can be seen by means of the light beam 5, drawn in generally, that shoulder areas 6 and neck areas 7 cannot be inspected. Thus, the inspection according to the prior art harbors the risk of an inadequate inspection result. The defects and contamination (F1, F2) in the areas there are shown by shading.

Figure 2:
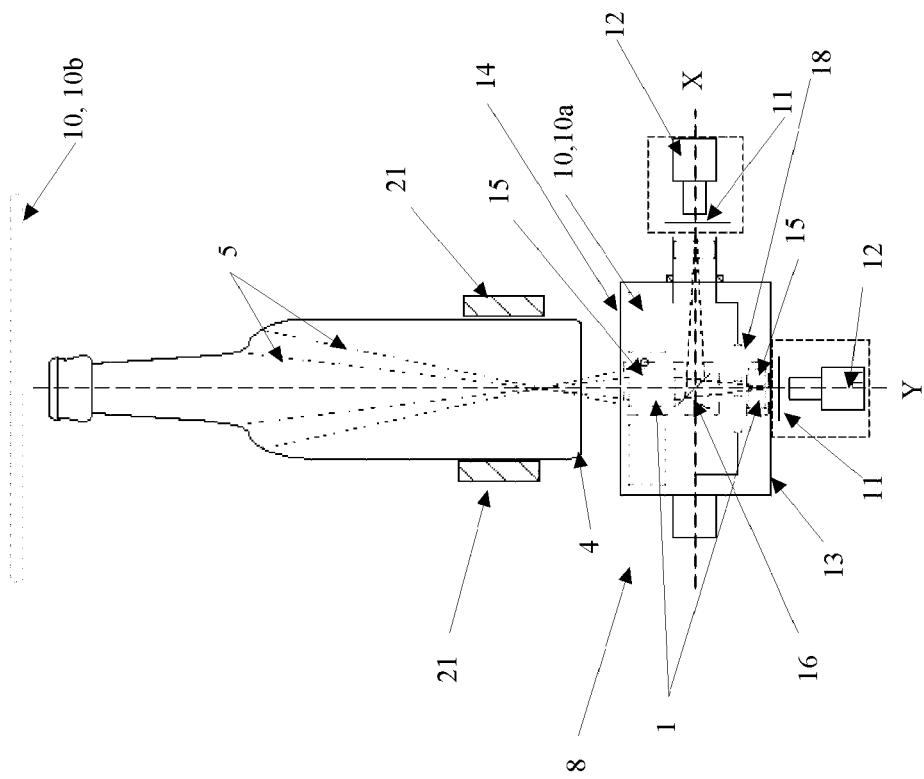
FIG. 2 shows an inspection device according to the present application in a side view.
Figure 3:
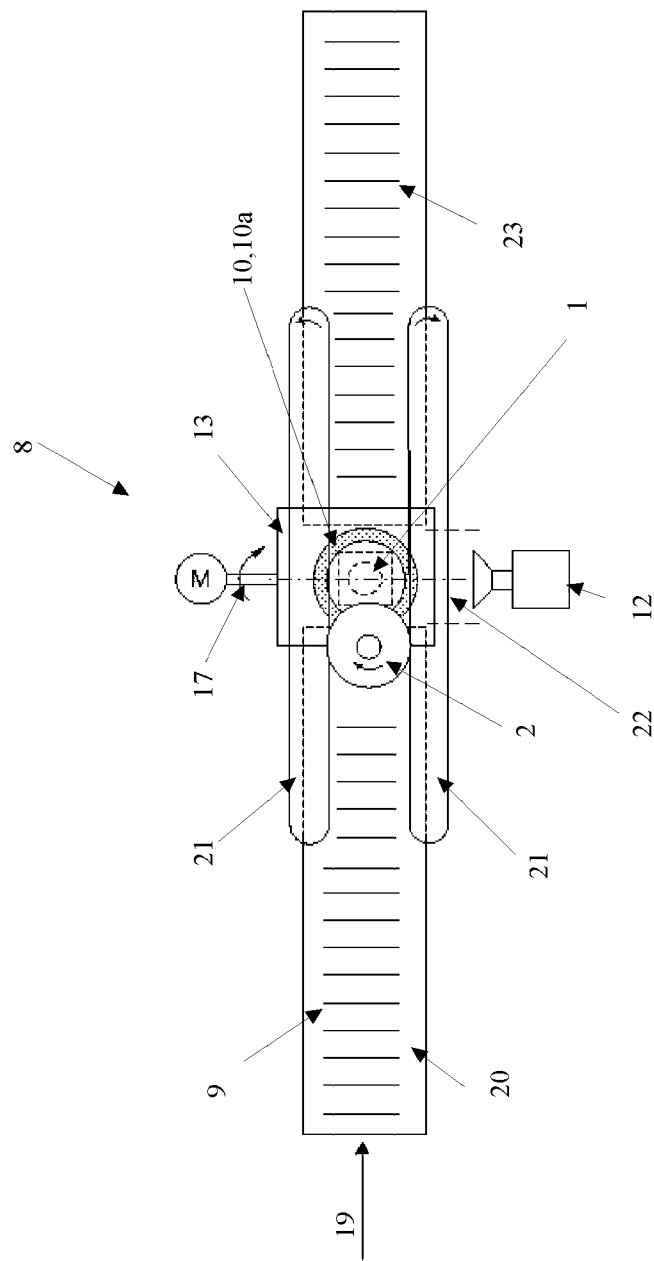
FIG. 3 shows the inspection device from FIG. 2 in a view from above.

FIG. 2 shows an inspection device 8 according to the present application in a side view, whereby the inspection device 8 is shown in a view from above in FIG. 3.

The inspection device 8 comprises at least one transport path 9 and has at least one illumination unit 10, one camera 12 and the optical structure 1. A transparent hollow body 13 mounted so that it is rotatable about a center axis X is provided, wherein said hollow body is arranged underneath a container 2 to be inspected. The optical structure 1 relative to the rotatable transparent hollow body 13 is arranged rigidly or in stationary manner inside the latter in such a way that the containers 2 to be inspected can be inspected by means of the at least one camera 12 through the container base 4 in the direction of the mouth 3.

The optical structure 1 inside the hollow body 13 has lens systems 15 and mirrors 16. The mirror 16 is in one possible embodiment embodied as a semi-transparent mirror.

The hollow body 13 has a drive shaft 17, on which a drive engages in a suitable manner. A first camera 12 with its optical axis is arranged congruently with the center axis X. The camera 12 arranged on the side is arranged underneath a zenith 14 of the hollow body 13. In the drawing level underneath the hollow body 13, a second camera 12 is arranged, which with its optical axis is parallel to or intermittently congruent with the vertical axis Y of the container 2 to be inspected. Optical filters 11 are also in each case assigned to the cameras 12.

Inside the hollow body 13, a field diaphragm 18 is also arranged between the lens systems 15.

For example, two illumination units 10 are provided, of which one illumination unit 10a is arranged inside the hollow body 13. The other illumination unit 10b is arranged outside the hollow body 13.

The illumination unit 10 arranged inside the hollow body 13 is made as a ring light illumination 10a, which concentrically encloses the optical structure 1. The ring light illumination 10a too is possibly arranged rigidly inside the hollow body 13. For the purposes of the present application, rigidly means that the hollow body rotates about its axis of rotation X or about its center axis X, while the optical structure 1 and the ring light illumination 10a do not rotate. Thus, the hollow body 13 rotates relative to the optical structure 1 and to the ring light illumination 10a.

The outer illumination unit 10 on the other hand is made as area lighting 10b. Both cameras 12 can be held in a transparent housing in at least one possible embodiment according to the present application.

FIG. 3 shows the inspection device 8 in a view from above with the transport path 9. The container 2 or the bottle 2 is on a conveyor belt 20 which moves the container 2 or the bottle 2 in the direction of the arrow 19. The container 2 or the bottle 2 is already in the operating area of perpendicular or substantially perpendicular lifting belts 21 and directly before or already partially over a gap 22 which is formed between the supply conveyor belt 20 and the removal conveyor belt 23.

Under this gap 22 is the schematically illustrated hollow body 13 which comprises the ring light illumination 10b and the optical structure 1. The camera 12 arranged on the side can likewise be seen. The container 2, held suspended, is transported past the optical unit 1.

In the example shown, the endlessly circulating lifting belts 21 arranged on the side are driven at different speeds so that the container 2 in the operating area of the lifting belts 21 rotates about its central vertical axis Y.

Figure 4:
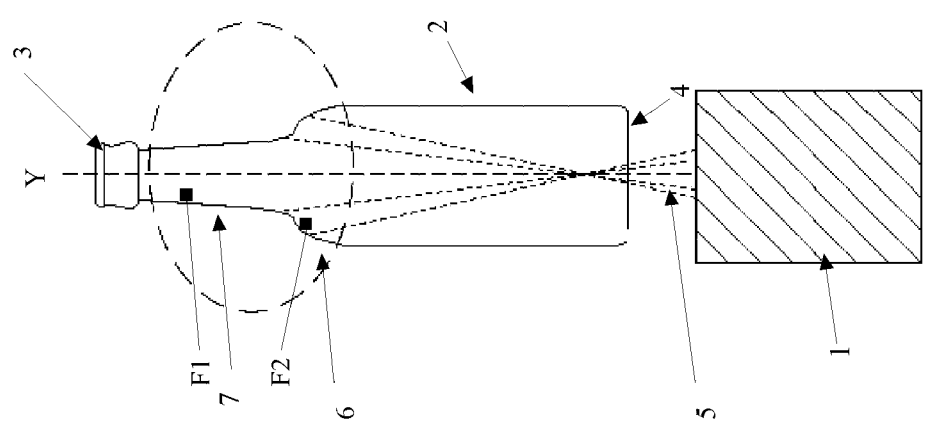
FIG. 4 shows the inspection device from FIG. 2 with the theoretical light beam.

It can now be seen in FIG. 4 that, due to the inspection from below, in one possible embodiment also the shoulder area 6 and the neck area 7 can be inspected.

On the hollow body 13, which can also be described as a glass or plastic cylinder, a cleaning unit can also be arranged for cleaning the exterior of the hollow body 13. Furthermore, a monitoring camera can be provided which for example inspects the outer circumference of the hollow body 13, and, if applicable, generates a signal when cleaning is required and/or desired, which is passed on to the cleaning unit by means of a control unit (not shown).

The angle of vision, i.e. in the case of the aperture angle of the lens likewise has an influence on the "reflection image." With a fixed focal length, the aperture angle is constant or substantially constant, whereas with zoom lenses the aperture angle is variable, and thus can be zoomed in or out, so that a change of image size arises.

To avoid and/or restrict and/or minimize an arched illumination from the hollow body, it can be possible to adapt the hollow body 13 accordingly in terms of its dimensions. It could be possible if the internal diameter of the hollow body 13 were possibly selected to be at least as big or even, depending on the bottle base concavity, slightly larger, whereby said internal diameter is the free passage or, better expressed, the inactive illumination part, where the illumination unit is designed as ring light illumination 24. Otherwise it can be that the illumination means reflect for example LEDs from the ring illumination 24 inside the smooth base area as rejects. This smooth/concave area of the container base 4 should however, because of the contrast for purposes of defect detection, remain dark/black. The imprints in the middle, base fluting in the edge area, or other defects or artifacts (typical base defects: chips (in German called mussels as they are generally the shape of mussels on the container or bottle base), cracks, fissures) which cause a light scatter in the base area of the container 2, can reflect in the image to be taken with the present application. Once again it would however also be useful if the internal diameter of the ring illumination 24 were selected to be not too big in relation to the container diameter, as otherwise no sufficient rejections occur in the edge area of the bottle (base fluting). The active area of the ring illumination 24 can, depending on the container diameter and the distance of the ring illumination 24 to the container 2, be designed clearly larger, limited to the maximum installation space. The active area is not quite so critical as the inactive area of the ring illumination 24.

With a container diameter of 60 millimeters, the dimensions can for example be as follows.

Inactive area ring illumination: min. 70 millimeters, active area 85 millimeters to 120 millimeters. The greater the container base diameter/distance of illumination to the container 2, the greater the inactive area or active area of the ring illumination 24 is. It is possible if the ratio between the container base diameter and the inactive area remains constant or substantially constant.

Figure 5:
FIG. 5 an image of the container's internal wall produced by means of the inspection device.
Figures 7A, 7B:
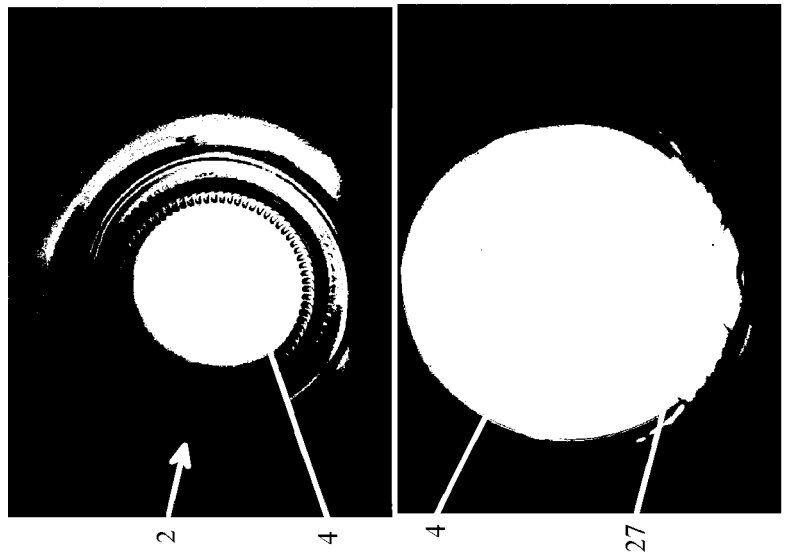
FIGS. 6, 7a, and 7b show comparative images, specifically an image of the container base produced by means of the inspection device (FIG. 6), and pictures of the container mouth (FIG. 7a) and container base (FIG. 7b) which was produced by means of an inspection device according to FIG. 1.
Figure 6:
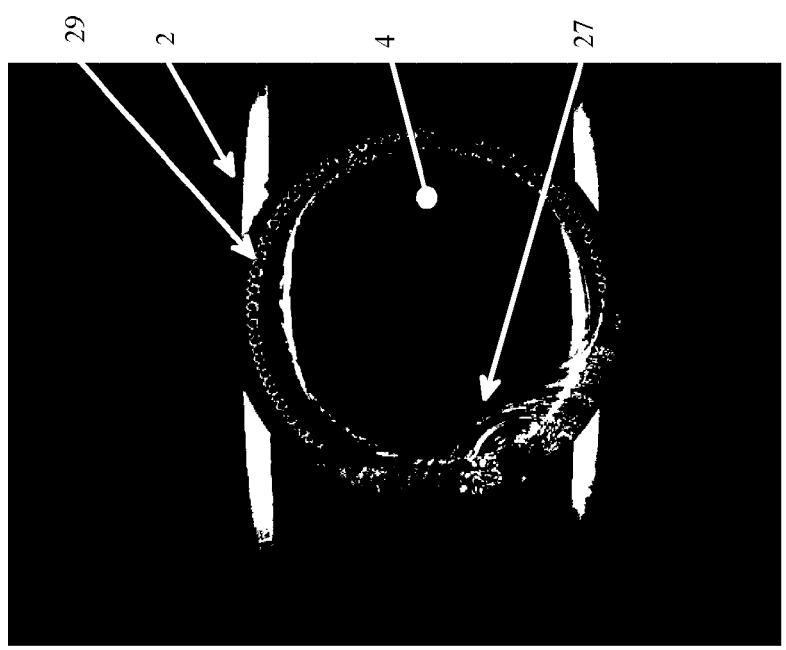

FIGS. 5 to 7 show real illustrations of the internal wall of a container and the container base, wherein the illustrations 5 and 6 were produced with the aforesaid inspection device and the illustrations 7a and 7b were produced by means of an inspection device known from the prior art. For a better illustration, the reference lines were made as black and white double arrows, which however point to the same characteristic in each case.

The container 2 shown in FIG. 5 has two embossings. A neck embossing 25 and a belly embossing 26 which are arranged on the container 2 in positions offset by 180 degrees. It can clearly been seen here that the two defects or areas of dirt (F1, F2) are depicted in sharp contrast despite the unfavorable position inside the container 2, namely in the shoulder area (F2) or slightly below the container mouth (F1).

It can also be seen from FIG. 5 that the relative position of the two embossings 25, 26 to each other or to the container seam 28 is likewise recognizable as it is sharply contrasted. It is thus possible to inspect and to monitor them, for example with regard to their position relative to each other or their size. The device allows this inspection in combination with the defect inspection or solely to check the embossing or seam.

As in this way the angular positions of an embossing and/or the container seam can be detected, these data can possibly be transmitted to a downstream unit or a handling machine, to control for example the direction for an angular rotation for a subsequent orientation in connection with labeling. In one possible embodiment of the method, the holding belts 21 or another suitable carrier element can be accelerated or slowed down in a controlled manner by means of these data on the angular position of the embossings so that the containers 2 are released from the holding belts 21 in a desired orientation. Moreover, the container seam 28 can be seen as a shaded line.

FIG. 6 shows the base inspection carried out in parallel or offset by milliseconds using a dark light method. A shard eruption 27 and the sharply contoured base corona 29 can be clearly seen. The shape of the base corona 29 and its surface geometry is depicted well and can be seen well so that it can even be used as a measure for the degree of wear of a container 2. This means that in the event of a loss of or degree of change to a pattern, the container 2 can be rejected.

In comparison with this, pictures of the container base 4, the shard eruption 27 and the base corona 29 can be seen which were generated with a camera arranged on the mouth side. With this, a clearly lesser contrast resolution may be achieved. This is quite considerable in one possible embodiment with regard to the detection of a shard eruption 27 (FIG. 7b); there the contours were flashed over to a large extent. Shard eruptions restricted to the area of the wall thickness, i.e. not as in this example protruding into the base surface, cannot be detected at all with a camera on the mouth side.

Thus, the device is also possibly suitable for detecting an embossing and marks which are arranged very closely on the base corona, such as for example in the case of marks which are made for quality assurance reasons, but which are not to adversely affect the appearance of the container.

Moreover the inspection device is outstandingly suitable for detecting and analyzing the axial symmetry of the entire bottle, such as the position of the mouth 3 to the center of gravity or the center of the container base or the central seam of a plastic bottle, such as in the case of a PET bottle, to the mouth 3 or the position of the central seam of the base of a plastic bottle to the other container base or base corona 29.

As previously stated, these inspections are carried out so to speak in parallel in one inspection stage and in a very compact inspection unit.

Figure 8:
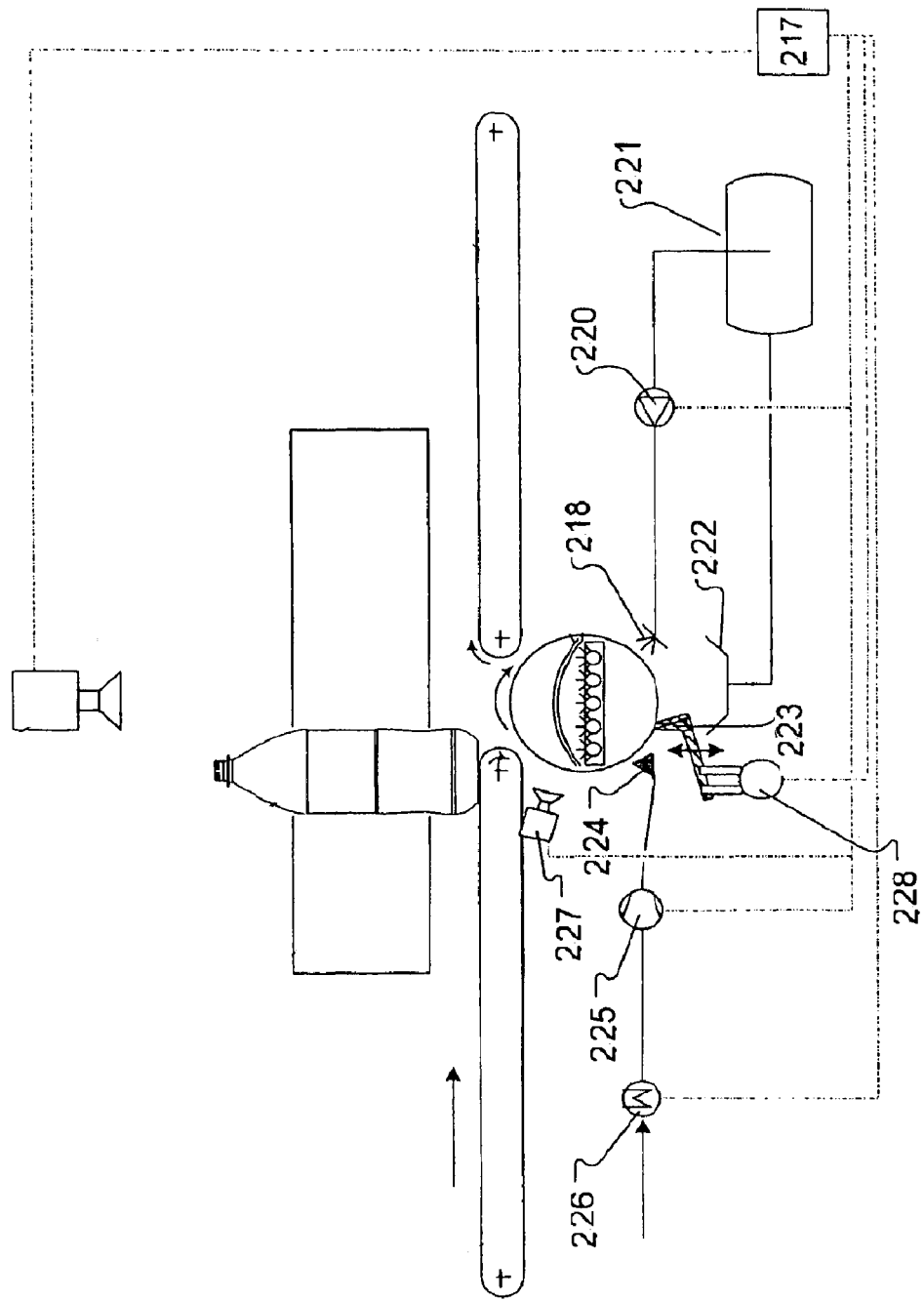
FIG. 8 shows a cleaning device for an inspection device.

FIG. 8 shows a side view of an inspection device according to U.S. Patent Publication 2011/0102782, which is incorporated by reference herein. Specifically, FIG. 8 shows an example of a cleaning device for cleaning a hollow body. A cleaning unit is located below the hollow body. The cleaning unit includes a spray head 218, a pump 220, a storage container 221, a collecting tray 222, a motor-driven pivotable scraper 223 and a drying unit. Actuated by the evaluating and control unit 217, the outside surface of the hollow body is sprayed sequentially by the spray head 218 by means of the pump 220. Prior to this in time or at the same time, the scraper 223, driven by the motor 228, is moved to the surface of the hollow body. The scraper 223 has double wiping lips, comparable to a windscreen wiper, and is produced from a silicone material. On account of said arrangement, part of the adhesion flows or drops from the deepest tube portion into the collecting tray 222. The remaining adhesions and moisture are removed by the scraper 223 and also drop into the collecting tray 222. The cleaning fluid is directed by means of a pipe line into the storage container 221, where it is available to be used again. A drying unit is located downstream of the scraper 223 in the direction of rotation, said drying unit including a hot air blower 224, which accomplishes the final drying of the cleaned outside surface of the hollow body. The compressor 225 connected to the hot air blower 224 and the associated heat unit 226 are also actuated by the evaluation and control unit 217. The surface of the hollow body can consequently be cleaned in an optimum manner. Continuously abradant elements or scrapers, which themselves result in contamination, are avoided. In the present example, the surface of the hollow body is monitored by the camera 227 which is downstream of the scraper 223 and of the hot air blower 224 in the direction of rotation. This corresponds to monitoring the cleaning performance of the cleaning unit.

The present application relates to an inspection device 8 comprising at least one transport path 9 and having at least one illumination unit 10, 10*a*, 10*b*, a camera 12 and also an optical structure 1, e.g. a mirror, wherein a transparent hollow body 13 is provided which is mounted so as to be rotatable about a center axis X and which is arranged underneath a container 2 to be inspected, such that the optical structure 1 is arranged rigidly inside the rotatable, transparent hollow body 13, such that the containers 2 to be inspected are able to be inspected, by means of the at least one camera 12, through the container base 4 in the direction of the mouth 3.

One feature or aspect of an embodiment is believed at the time of the filing of this patent application to possibly reside broadly in an inspection device comprising at least one transport path 9 and having at least one illumination unit 10, 10*a*, 10*b*, one camera 12 and one optical structure 1, wherein a transparent hollow body 13 is provided which is mounted so as to be rotatable about a center axis X, said hollow body being arranged underneath a container 2 to be inspected wherein the optical structure 1 relative to the rotatable transparent hollow body 13 is arranged rigidly inside the latter in such a way that the containers 2 to be inspected can be inspected by means of the at least one camera 12 through the container base 4 in the direction of the mouth 3.

Another feature or aspect of an embodiment is believed at the time of the filing of this patent application to possibly reside broadly in the inspection device, wherein the illumination unit 10, 10*a* is made as a ring light illumination 10*a* which is arranged inside the hollow body 13.

Yet another feature or aspect of an embodiment is believed at the time of the filing of this patent application to possibly reside broadly in the inspection device, wherein the illumination unit 10, 10*a* is made as ring light illumination 10*a* which is arranged concentrically around the optical structure 1 inside the hollow body 13.

Still another feature or aspect of an embodiment is believed at the time of the filing of this patent application to possibly reside broadly in the inspection device, wherein the illumination unit 10, 10*b* is arranged as area lighting outside the hollow body 13.

A further feature or aspect of an embodiment is believed at the time of the filing of this patent application to possibly reside broadly in the inspection device, wherein the illumination unit 10, 10*a*, 10*b* provided is both a ring light illumination 10*a* inside the hollow body 13 and also area lighting 10*b* outside the hollow body 13, wherein the container 2 to be inspected is illuminated with illumination units 10, 10*a*, 10*b* of different color spectra, and wherein the container 2 to be inspected can be inspected by the dark field method and/or by the transmitted light method.

Another feature or aspect of an embodiment is believed at the time of the filing of this patent application to possibly reside broadly in the inspection device, wherein the optical structure 1 comprises lens systems 15 and mirrors 16.

Yet another feature or aspect of an embodiment is believed at the time of the filing of this patent application to possibly reside broadly in the inspection device, wherein the optical structure 1 comprises semi-transparent mirrors 16.

Still another feature or aspect of an embodiment is believed at the time of the filing of this patent application to possibly reside broadly in the inspection device, wherein at least one camera 12 with its optical axis is congruent with the center axis X of the hollow body 13 so that the at least one camera 12 is arranged to the side of the hollow body 13.

A further feature or aspect of an embodiment is believed at the time of the filing of this patent application to possibly reside broadly in the inspection device, wherein the at least one camera 12 is arranged underneath the hollow body 13.

Another feature or aspect of an embodiment is believed at the time of the filing of this patent application to possibly reside broadly in a method for inspecting containers 13 with at least one illumination unit 10 and at least one camera 12, wherein at least one camera 12 is oriented directly or by means of mirrors from below onto the base 4, and wherein the inner surface of the container 2 and/or the position and/or the geometry of the mouth 3 and/or the container symmetry is detected through the container base.

Yet another feature or aspect of an embodiment is believed at the time of the filing of this patent application to possibly reside broadly in the method, wherein the container 2 is transported in a suspended manner.

Still another feature or aspect of an embodiment is believed at the time of the filing of this patent application to possibly reside broadly in the method, wherein for this an inspection device according to the present application is used.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

The following patents, patent applications or patent publications, are hereby incorporated by reference as if set forth in their entirety herein except for the exceptions indicated herein: EP 0 894 544 A, having the title "Inspection machine for testing bottles or the like," published on Feb. 3, 1999; DE 10 2005 057 872 A1, having the title "Inspection machine," published on Jun. 14, 2007; and EP 2 229 582 A1, having the title "INSPECTION DEVICE WITH ROTATABLE LIGHTING ELEMENT HOUSING," published on Sep. 22, 2010.

All of the patents, patent applications, patent publications, and other documents, except for the exceptions indicated herein, which were cited in the German Office Action dated Jun. 19, 2013, and/or cited elsewhere, as well as the German Office Action document itself, are hereby incorporated by reference as if set forth in their entirety herein except for the exceptions indicated herein, as follows: WO 2009/056188, having the title "INSPECTION DEVICE WITH ROTATABLE LIGHTING ELEMENT HOUSING," published on May 7, 2009; DE 103 10 273, having the title "Automatic inspection of the inside of transparent packaging, e.g. bottles with a narrow throat, whereby inspection is carried out using cameras and matching light sources arranged above and below the containers," published on Sep. 23, 2004; DE 10 2004 051 961, having the title "Device for inspecting foreign bodies in filled container comprises vibration unit for vibrating container," published on May 4, 2006; and DE 10 2010 018 824, having the title "Device for inspecting turbid liquids of glass bottles in beverage manufacturing industry, has illumination device for illuminating bottom portion and base surface of containers, and image recording device for monitoring base surface," published on Nov. 3, 2011.

All of the patents, patent applications, patent publications, and other documents, except for the exceptions indicated herein, which were cited in the International Search Report dated Oct. 25, 2013, and/or cited elsewhere, as well as the International Search Report document itself, are hereby incorporated by reference as if set forth in their entirety herein except for the exceptions indicated herein, as follows: JP 2006 201003, having the title "DEVICE OF INSPECTING FOREIGN MATTER IN CONTAINER," published on Aug. 3, 2006; DE 10 2006 062575, having the title "Device for inspecting container base of containers, has holding device, which transports container over support plate and viewing window is arranged below container base and has observation device, with which container base is inspected," published on Mar. 27, 2008; US 2011/102782, having the title "INSPECTION DEVICE WITH ROTATABLE LIGHTING ELEMENT HOUSING," published on May 5, 2011; and JPH04216445, having the title "DEVICE FOR INSPECTING BOTTLE," published on Aug. 6, 1992.

The corresponding foreign and international patent publication applications, namely, Federal Republic of Germany Patent Application No. 10 2012 016 342.8, filed on Aug. 20, 2012, having inventors Wolfgang SCHORN and Carsten BUCHWALD, and DE-OS 10 2012 016 342.8 and DE-PS 10 2012 016 342.8, and International Application No. PCT/EP2013/002382, filed on Aug. 8, 2013, having WIPO Publication No. WO 2014/029470 and inventors Wolfgang SCHORN and Carsten BUCHWALD, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2013/002382 and German Patent Application 10 2012 016 342.8, is solely for the purposes of providing a basis of correction of any wording in the pages of the present application, which may have been mistranslated or misinterpreted by the translator, and to provide additional information relating to technical features of one or more embodiments, which information may not be completely disclosed in the wording in the pages of this application.

Statements made in the original foreign patent applications PCT/EP2013/002382 and DE 10 2012 016 342.8 from which this patent application claims priority which do not have to do with the correction of the translation in this patent application are not to be included in this patent application in the incorporation by reference.

Any statements about admissions of prior art in the original foreign patent applications PCT/EP2013/002382 and DE 10 2012 016 342.8 are not to be included in this patent application in the incorporation by reference, since the laws relating to prior art in non-U.S. Patent Offices and courts may be substantially different from the Patent Laws of the United States.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL LIST OF
NOMENCLATURE

1 Optical structure
2 Container
3 Mouth

4 Container base
5 Light beam
6 Shoulder area
7 Neck area
8 Inspection device
9 Transport path
10 Illumination units (also 10a, 10b)
11 Filter
12 Camera
13 Hollow body
14 Zenith of 13
15 Lens systems
16 Mirrors/semi-transparent mirrors
17 Drive shaft
18 Field diaphragm
19 Transport direction arrow
20 Conveyor belt
21 Lifting belts
22 Gap
23 Conveyor belt
24 Ring illumination
25 Neck embossing
26 Breast embossing
27 Shard eruption
28 Container seam
29 Base corona
F1 Defect, contamination in the neck area
F2 Defect, contamination in the shoulder area

What is claimed is:

1. A container inspection arrangement for inspecting glass and/or plastic containers, said container inspection arrangement comprising:
 a transport arrangement to move containers along a transport path to, through, and from an inspection area;
 at least one illumination unit to illuminate containers;
 a hollow body and a drive unit connected to said hollow body to rotate said hollow body about a central axis of said hollow body;
 said hollow body being disposed at said inspection area such that said hollow body is nearer a bottom of a container than a mouth of the container upon the container being in said inspection area;
 an optical structure being mounted in a stationary manner within said hollow body such that said optical structure does not move with said hollow body upon rotation of said hollow body;
 at least one camera being disposed to receive light via said optical structure to obtain images of at least one of: a bottom portion of the container and a body portion of the container, as viewed from the bottom of the container toward the mouth of the container; and
 said at least one illumination unit comprises a ring-shaped light disposed inside said hollow body.

2. The container inspection arrangement according to claim 1, wherein said hollow body is disposed at said inspection area such that said hollow body is underneath a container upon the container being in said inspection area.

3. The container inspection arrangement according to claim 2, wherein said ring-shaped light is disposed substantially concentrically around said optical structure.

4. The container inspection arrangement according to claim 3, wherein said at least one illumination unit also comprises an additional light disposed as area lighting outside said hollow body.

5. The container inspection arrangement according to claim 4, wherein:
 said ring-shaped light and said additional light are configured to emit light of different color spectra; and
 the container inspection arrangement is configured to inspect containers by at least one of: the dark field method and the transmitted light method.

6. The container inspection arrangement according to claim 5, wherein said optical structure comprises at least one lens system and at least one mirror.

7. The container inspection arrangement according to claim 6, wherein said at least one mirror is semi-transparent.

8. The container inspection arrangement according to claim 7, wherein:
 said at least one camera comprises a first camera and a second camera; and
 said second camera is disposed beside said hollow body and is oriented with its optical axis substantially parallel to the center axis of said hollow body.

9. The container inspection arrangement according to claim 8, wherein said first camera is disposed below said hollow body and is oriented with its optical axis substantially perpendicular to the center axis of said hollow body, which hollow body is substantially cylindrical.

10. The container inspection arrangement according to claim 1, wherein said at least one camera is disposed to receive light via said optical structure to obtain images of both the bottom portion of the container, and a neck area and a shoulder area of the container.

11. The container inspection arrangement according to claim 1, wherein said transport arrangement comprises:
 a first conveyor configured to move containers to the inspection area;
 a second conveyor configured to move containers from the inspection area;
 said first conveyor and said second conveyor are separated from one another by a gap at the inspection area; and
 a third conveyor configured to carry containers over the gap from said first conveyor to said second conveyor to permit inspection of the container from under the container at the inspection area.

12. A method of inspecting glass and/or plastic containers using a container inspection arrangement, said method comprising:
 transporting a container using a transport arrangement along a transport path to an inspection area;
 illuminating the container using at least one illumination unit;
 transmitting a portion of the light that illuminates the container through a hollow body, which hollow body is rotatable about a central axis thereof using a drive unit connected thereto, and which hollow body is disposed at said inspection area such that said hollow body is nearer a bottom of the container than a mouth of the container;
 transmitting the portion of the light to an optical structure, which optical structure is mounted in a stationary manner within said hollow body such that said optical structure does not move with said hollow body upon rotation of said hollow body;
 receiving the portion of the light using at least one camera, and thereby obtaining images of at least a portion of the container, as viewed from the bottom of the container toward the mouth of the container;
 detecting at least one of: the inner surface of the container, the position of the mouth of the container, the geometry of the mouth of the container, and the symmetry of the container; and said at least one illumination unit comprises a ring-shaped light disposed inside said hollow body.

13. The method according to claim 12, wherein:
said method further comprises moving the container in a suspended manner to an inspection area; and
said hollow body is disposed at said inspection area such that said hollow body is underneath a container upon the container being in said inspection area.

14. The method according to claim 13, wherein said method comprises using said ring-shaped light to generate light in a dark field inspection of at least the bottom surface of the container.

15. The method according to claim 14, wherein said ring-shaped light is disposed substantially concentrically around said optical structure.

16. The method according to claim 15, wherein said at least one illumination unit also comprises an additional light disposed as area lighting outside said hollow body, and said method comprises using said additional light to generate light in a transmitted light inspection of at least a portion of the container.

17. The method according to claim 16, wherein:
said ring-shaped light and said additional light are configured to emit light of different color spectra;
said optical structure comprises lens systems and at least one mirror; and
said method further comprises transmitting light from one to another of said lens systems.

18. The method according to claim 17, wherein:
said at least one mirror is semi-transparent;
said at least one camera comprises a first camera and a second camera;
said second camera is disposed beside said hollow body and is oriented with its optical axis substantially parallel to the center axis of said hollow body; and
said method further comprising reflecting a portion of the portion of the light with said mirror to said second camera.

19. The method according to claim 18, wherein:
said first camera is disposed below said hollow body and is oriented with its optical axis substantially perpendicular to the center axis of said hollow body; and
said method further comprising transmitting another portion of the portion of the light through said mirror to said first camera.

20. The method according to claim 12, wherein:
the container comprises a neck area and a shoulder area; and
said step of detecting comprises detecting both the bottom portion of the container, and a neck area and a shoulder area of the container.

* * * * *